United States Patent [19]

Hanneman

[11] 4,012,141
[45] Mar. 15, 1977

[54] IDENTIFICATION OF GEMSTONES BY RELATIVE REFLECTANCE MEASUREMENTS COUPLED WITH A SCALE CALIBRATED IN GEM NAMES

[76] Inventor: Walter William Hanneman, 18675 Sheffield Road, Castro Valley, Calif. 94546

[22] Filed: Mar. 10, 1976

[21] Appl. No.: 665,573

Related U.S. Application Data

[63] Continuation of Ser. No. 524,647, Nov. 18, 1974, abandoned.

[52] U.S. Cl. .............................. 356/30; 356/209; 356/212
[51] Int. Cl.² ........................................ G01N 21/48
[58] Field of Search ............. 356/30, 31, 128, 209, 356/212

[56] References Cited

UNITED STATES PATENTS 3,751,162   8/1973   Long .................................. 356/30

Primary Examiner—Eugene R. LaRoche

[57] ABSTRACT

This invention embodies a novel concept in the confirmation of the identification of faceted gemstones and an instrument which makes this concept practical and useful.

The concept is that it is not necessary to determine the refractive index ($n_D$) of a gem in order to identify it if one has an instrument capable of determining the ability of that gem to reflect light relative to the ability of other gems to reflect light. With this invention, an individual completely unskilled in the science of gemology, can almost instantaneously determine if a gem is indeed what it is purported to be.

8 Claims, 4 Drawing Figures

IDENTIFICATION OF GEMSTONES BY RELATIVE REFLECTANCE MEASUREMENTS COUPLED WITH A SCALE CALIBRATED IN GEM NAMES

This is a continuation of application Ser. No. 524,647, filed Nov. 18, 1974, now abandoned.

BACKGROUND

The intrinsic value of faceted gemstones is a well recognized fact and commercial transactions in which these items change ownership may involve considerable sums of money. For this reason it is imperative that the prospective buyer have a means of ascertaining whether or not the gems in question are indeed what the seller claims them to be.

Because of their highly polished surfaces, any tests the prospective buyer may be allowed to make must be completely non-destructive, and this limitation has resulted in the development of the science of gemology. Heretofore the most important instrument of the gemologist for identification work has been the refractometer. This instrument in the hands of a trained gemologist is capable of accurately indicating the refractive index ($n_D$) of the gem. When this value has been determined, the trained gemologist refers to reference books to determine those possible gems which have the determined value of $n_D$. Accurate values of $n_D$ have been determined and recorded for all gemstones. Depending upon other characteristics — e.g., color, pleochroism, or birefringence of those possibilities — he can either make a firm identification or determine what other test he must make.

For the confirmation of the purported identity of most common gems, the $n_D$ value is usually sufficient, as those gems most similar in appearance usually have significantly different $n_D$ values.

The range of the gemologist's refractometer is greatly limited by the requirements of its optical system (which determines the critical angle but converts that value into $n_D$ which is read on the scale) and this instrument cannot be used to determine $n_D$ values above 1.81. Many important gems have higher values of $n_D$.

About 1825 Fresnel and Snell developed equations relating the ratio of reflected light:incident light to the index of refraction ($n_X$ where X is the wavelength of incident light) of a transparent solid.

Attempts have been made to construct refractometers based on this principle (Fresnel's) as they should be capable of measuring the refractive index ($n_D$) of all gems.

The purpose of such a refractometer would be to accurately measure $n_D$ so that this value can be used to make a judgement based upon the published reference values for the minerals. Without an accurate value of $n_D$, erroneous conclusions will be drawn.

A refractometer of this type must use monochromatic sodium light in order to get accurate values of $n_D$. The index of refraction (n) of a gem material varies with the wavelength of the light used for the measurement. The term used to describe this change is dispersion. Dispersion is defined as ($n_C - n_F$) where C and F represent wavelengths corresponding to the F (blue) and C (red) lines of the hydrogen spectrum. Dispersion is the property which imparts the flash of "fire" in a diamond. Over reasonably short ranges the slope of $$\frac{\Delta n}{\lambda}$$

is constant and one can estimate the correction required to convert $n_X$ (the value determined by use of a different light source than a sodium lamp) to the value $n_D$ which is needed to confirm an identification.

$$n_D = n_X + (X-590) \frac{(n_C - n_F)}{(486-656)}$$

Since the value ($n_C - n_F$) is different for each gem and ranges from less than 0.01 to over 0.30, this correction factor becomes increasingly important as X deviates from 590 nm (D line of sodium).

Because of the dependence of the correction factor on the dispersion, it is impossible to convert an $n_X$ value to an $n_D$ value on an unknown specimen. Consequently it is impossible to construct a refractometer based upon Fresnel's equations which can give accurate $n_D$ values unless a light source of 590 nm is used. Because of the need to make very accurate measurements of $n_D$ and the subsequent interpretation of that value, it has been impossible for the unskilled individual to make accurate gem identifications. As a result, he must rely on the honesty of the seller to provide the correct identification. Because of this fact alone, great numbers of citizens each year buy gems of quartz under the mistaken impression that they are purchasing topaz. The problem is even greater in foreign countries where a visitor is offered "rare native stones at good prices". Upon returning with his purchases he is told by the gemologist that he has purchased "junk at inflated prices".

The commercial gem buyer usually has to travel to foreign lands to purchase gems near their source. In order for him to confirm the identity of the rare or unusual gems offered to him, it is necessary for him to carry his sophisticated equipment with him at a considerable inconvenience. Both the gem dealer and the untrained gem buying citizen have need for an instrument which is easy to carry, simple to operate and can accurately confirm or deny the validity of a purported identification.

This invention is based on the heretofore unrecognized concept that gem identifications can be confirmed by optical means without the determination of the refractive index. In order to perform this task, this instrument provides means for sensing an optical property which is different for each gem. This instrument therefore provides a means of relating that sensation into the name of the gem. Reflectivity is the property used in this invention. Fresnel's equation states that if a beam of light is directed onto the surface of a gem, the proportion of that beam which is reflected depends upon the index of refraction ($n_X$) of the gem at the wavelength of light used. However, due to dispersion, $n_X$ cannot be converted to $n_D$ and $n_X$ is in itself meaningless as $n_X$ has not been determined for the gems and so it cannot be used by the gemologist. One other limiting factor relating to the construction of a refractometer using Fresnel's formula is the fact that in order to determine the ratio, both the amount of incident and reflected light must be determined. If only the reflected light is determined, then the light source must be so focused that all of the incident light strikes the gem and reflections come from no other source. This requirement will require accurate alignment and focusing of the light beam along with the associated manufacturing costs. The ability to focus the light beam will determine the surface of the gem which must be exposed to the beam. This in turn limits the utility of the instrument to measure the $n_x$ of small gems.

SUMMARY

This invention recognizes the above facts and consists of an instrument which, although based on reflectance meaasurements, is not based on Fresnel's formula and does not determine the index of refraction ($n_x$) of the gem. It eliminates the necessity of accurate focusing of the light beam and thereby makes possible the identification of extremely small gems. It makes it possible for individuals possessing no knowledge whatsoever of gemology to accurately confirm the identification of all gems for which it is calibrated.

This invention is based on the following concepts.

1. The amount of an incident beam of light reflected from the surfaces of polished gems is different for each gem and is dependent upon the incident angle, the wavelength of light and the particular gem.
2. This instrument consists of a light source, a baseplate surface with a hole in it, and a sensor to measure the reflected light, all in fixed positions. The sensor is connected to a meter to provide a visual display of the sensor response. This setup will give a sensor response depending on the baseplate's ability to reflect light. The sensor response to this surface is called the background.
3. When a gem is placed over the hole, the sensor notes an increase in reflected light over the background. This increase in reflected light will be different for each gem and the total response of the sensor will be different for each gem.
4. Identifications are made by constructing a unique scale for the instrument which is calibrated, not in numerical values of any optical property of the gems, but in a graphical form of ranges in which the meter needle will fall for the different gems. The net result being an instrument which provides the identification of the gem.
5. The meter reading measures the sensor response which is determined by a combination of the background reflectance, size of the hole, nature of the gem, angle of the incident light, the wavelength of the incident light and the intensity of the light source.

The fact that the scale indicates a range of meter needle positions for each gem is significant and is the unique feature which makes it possible for this invention to work in the hands of a completely unskilled individual.

The minerals from which most gems are fashioned have more than one optic axis and each axis shows a different $n_D$. A gem cut from such a mineral will show an apparent $n_D$ which is somewhere between the extreme values of the axes.

The effects of this spread of $n_D$ values are apparent in the relative reflectance measurements made by this invention. Consequently the relative needle readings fall over a range of values. By constructing this scale to reflect this range, it is possible for an unskilled operator to identify gems on the basis of their optical properties.

Thus this instrument allows a prospective gem buyer to quickly answer a question such as whether the topaz offered to him is indeed a topaz or merely quartz because the scale of this instrument is graduated in the names of gems, i.e., answers.

Figure 1:
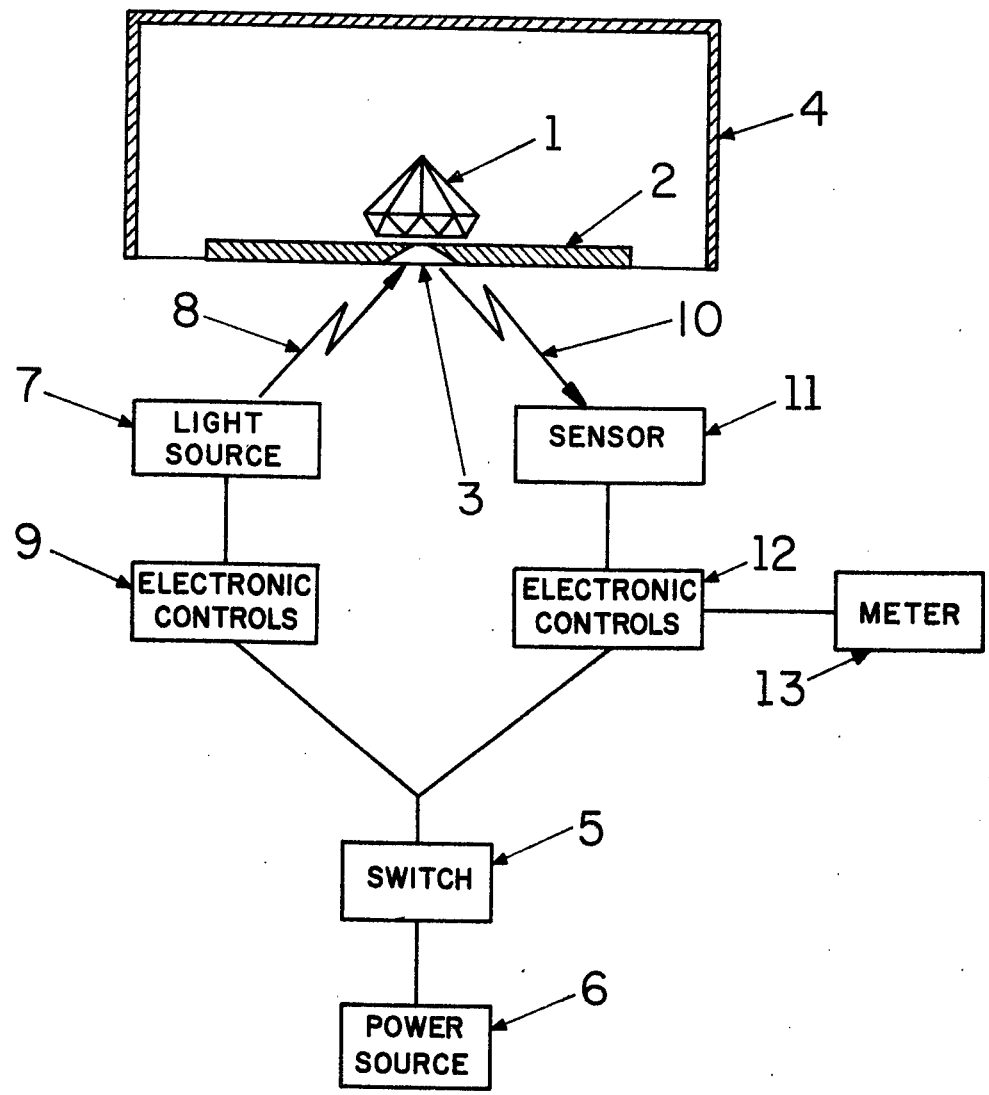
FIG. 1 is a diagram of the instrument of this invention.

The polished gem 1 is placed on the baseplate 2, making certain the hole 3 in the baseplate is completely covered. In order to eliminate external light from entering the precalibrated system, an opaque cover 4 is placed over the gem on the baseplate. In order to obtain an identification, the switch 5 is closed to provide energy from a power source 6 and cause the light source 7 to radiate energy 8 in the direction of the hole. The intensity of the light source is regulated by the required electronic resistors and circuits 9 depending upon the type of power supply and light source utilized in a particular instrument. The reflected rays 10 are intercepted by the sensor 11 which results in a response which is converted by the required electronic circuits 12 into a visual response on the meter 13.

It is recognized that any means of directing the light source, such as lenses or appertures, which cause a greater portion of the incident light to strike the hole 3 where the gem 1 is placed as well as any means, such as roughened surfaces, choice of materials of construction or coatings with light absorbing materials, which will reduce the intensity of background radiation will serve to increase the sensitivity of this invention. However, it is not imperative that all or even a major portion of the output of the light source strike the gem.

The reflection of radiant energy from a polished surface is a basic characteristic of the interaction between energy and matter. As such, it is not limited to certain wavelengths. For that reason the light source 7 may emit electromagnetic radiant energy ranging from the ultra violet to the micro wave region. Sources emitting wavelengths near the D line of sodium (yellow) would be advantageous for instruments to be used by one likely to encounter stones for which the instrument is not calibrated as the effect of dispersion on the estimation of refractive index is minimized. For general purposes, longer wavelengths in the infra red region are preferred as the effects of surface roughness due to a relatively poor polish on the gem are minimized.

The power source 6, electronic resistors and/or circuits 9, sensor 11 electronic circuits 12 and meter 13 are all composed of standard electronic components and will be determined by the choice of the incident light source 7.

A typical infra red light source 7 is represented by a GaAs light emitting diode and the sensor 11 by a silicon NPN phototransistor. A resistor 9 is used to fix the source 7 output and a standard transistor circuit 12 used to convert the sensor 11 response to a reading on an ammeter 13. The power source 6 may be a 9V battery. An alternate circuit 9 selectable by a switch may be utilized to provide a two range instrument by altering the source output.

Figure 2:
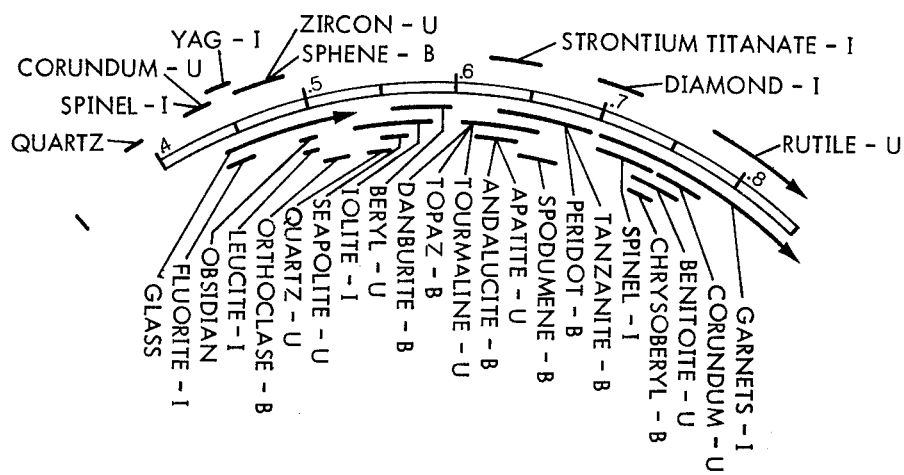
FIGS. 2, 3 and 4 are diagrams of typical meter scales used in this invention.
Figure 3:
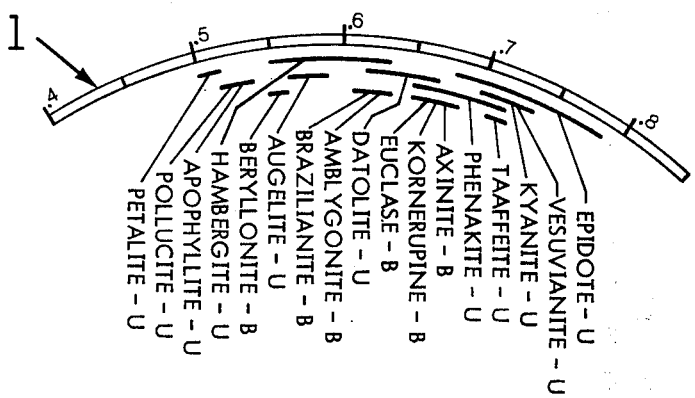
Figure 4:
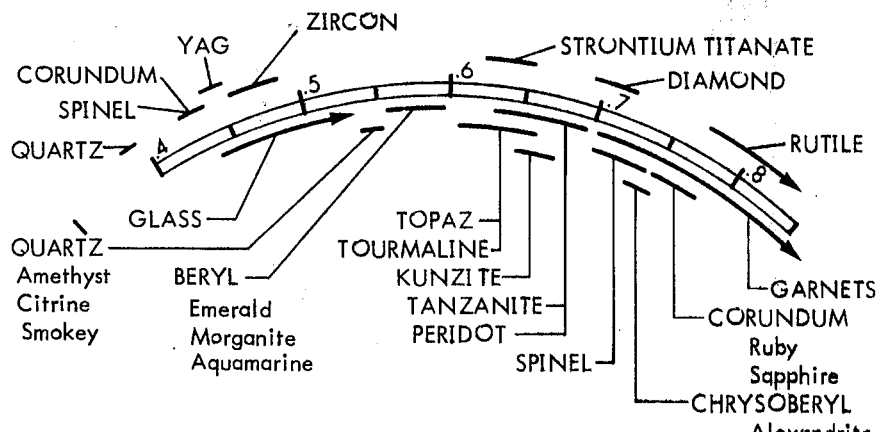

FIGS. 2, 3, and 4 show diagrams of typical scales. These scales are calibrated so as to read directly in the name of the mineral or minerals which when placed over the baseplate hole will produce a meter needle position corresponding to the dark arcs which are connected to the names by the narrow straight lines.

The graduated scale 1 shown in FIG. 2 represents an aid for approximating the RI value of an unknown for which the expected range on the meter has not been designated. It is based on the known wavelength of a particular light source and an assumed intermediate value for dispersion. In order to assure the recognition that this is only an approximate value, the scale is graduated from 0.4 to 0.8. Approximation of refractive index is made by adding 1.0 to the meter needle reading on this scale.

What is claimed is:

1. An instrument for identification of polished gemstones, comprising:
   a plate having a small hole therethrough, said plate being adapted to support a gemstone on the top thereof with a polished surface of said gemstone positioned over said hole;
   means for emitting light positioned under said plate so that light emitted thereby strikes an area of the bottom of the plate, said hole being included in said area, whereby the amount of light reflected from said area depends upon the presence or absence of a gemstone over said hole, and upon the reflectance of any gemstone so present;
   means for receiving light reflected from said area and for converting the amount of light received to an electrical signal;
   a meter having a scale calibrated in accordance with the relative reflectances of various gemstones; and
   means for connecting the electrical signal to said meter, whereby said meter provides an indication of the identity of a gemstone positioned over said hole.

2. An instrument as set forth in claim 1 which operates on any wavelength of radiant energy or combination of wavelengths between the ultra violet region and the infrared region of the electromagnetic spectrum inclusive.

3. An instrument as set forth in claim 1 which uses a light emitting diode as a light source and a phototransistor as a sensor.

4. An instrument as set forth in claim 1 which uses an infrared light emitting diode as a light source and a phototransistor as a sensor.

5. An instrument as set forth in claim 1 in which said meter is provided with a scale so calibrated that the position of the meter needle indicates directly the possible minerals or gems, for which the scale is calibrated.

6. An instrument as set forth in claim 1 having a single scale covering the entire range of responses possible for the known gemstones.

7. An instrument as set forth in claim 1 having multiple range scales, one of which covers the entire range, the other scales expand the regions where most of the gem responses fall.

8. A method of identifying a gemstone, comprising:
   placing, one at a time, a plurality of gemstones of known identity over a hole in a baseplate;
   illuminating with radiant energy the bottom of said baseplace in the vicinity of said hole such that at least a substantial portion of said energy enters said hole to strike the gemstones;
   measuring, for each gemstone placed over the hole, the amount of energy reflected from said baseplace and gemstone, whereby the relative reflectance of each gemstone is established;
   deflecting the needle of a meter in proportion to the so established relative reflectance of each gemstone and calibrating the scale of the meter in accordance therewith;
   placing a gemstone of unknown identity over said hole;
   performing upon the gemstone of unknown identity the illuminating, measuring and deflecting steps recited above; and
   comparing the deflection of the meter needle to said calibrated scale to establish the identity of said gemstone.

* * * * *